12) United States Patent
Hen et al.

(10) Patent No.: US 11,554,137 B2
(45) Date of Patent: *Jan. 17, 2023

(54) COMPOSITION AND METHOD FOR ARRESTING BLOOD FLOW AND FOR FORMING A PERSISTENT MICROBIAL BARRIER

(71) Applicant: Biolife, L.L.C., Sarasota, FL (US)

(72) Inventors: John Hen, Bradenton, FL (US); John Alfred Thompson, Nassau (BS); Talmadge Kelly Keene, Apollo Beach, FL (US); Mark Travi, Venice, FL (US)

(73) Assignee: Biolife, L.L.C., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/147,143

(22) Filed: Jan. 3, 2014

(65) Prior Publication Data
US 2014/0120052 A1  May 1, 2014

Related U.S. Application Data

(62) Division of application No. 12/900,170, filed on Oct. 7, 2010, now abandoned.

(51) Int. Cl.
A61K 31/795 (2006.01)
B01J 39/20 (2006.01)
B01J 39/05 (2017.01)

(52) U.S. Cl.
CPC ............ A61K 31/795 (2013.01); B01J 39/05 (2017.01); B01J 39/20 (2013.01)

(58) Field of Classification Search
CPC .......... A61K 31/795; B01J 39/05; B01J 39/20
See application file for complete search history.

(56) References Cited

U.S. PATENT DOCUMENTS

| 4,938,958 | A | * | 7/1990 | Niira et al. | 424/78.1 |
| 6,187,347 | B1 | | 2/2001 | Patterson et al. | |
| 6,472,358 | B1 | | 10/2002 | Richter et al. | |
| 6,531,519 | B2 | | 3/2003 | Patil | |
| 7,147,845 | B2 | | 12/2006 | Capelli | |
| 8,110,208 | B1 | | 2/2012 | Hen | |
| 2002/0141964 | A1 | * | 10/2002 | Patterson | A61K 31/14 424/78.1 |
| 2007/0269499 | A1 | * | 11/2007 | Hen et al. | 424/445 |
| 2008/0181950 | A1 | | 7/2008 | Bates et al. | |
| 2009/0202615 | A1 | | 8/2009 | Rodeheaver et al. | |
| 2015/0165095 | A1 | | 6/2015 | Mansour et al. | |

OTHER PUBLICATIONS

Gethin. Wounds UK. 2007; 3(3): 52-56.*
Smith and Nephew, "The Relationship Between pH and Wound Healing", http://www.smith-nephew.com/new-zealand/healthcare/products/product-types/protease-modulating-cream/cadesorb-/cadesorb-simple-science/the-relationship-between-ph-and-wound-healing/.
Basavraj S. Nagoba, et al., "Wounds", vol. 27, Issue 1, Jan. 2015, pp. 5-11.
Nae Matsuda et al., "Colloids and Surfaces B: Biointerfaces", vol. 7, Issues 1-2, (1996), pp. 91-100.
Human Physiology—Blood and Body Defenses, http://people.eku.edu/ritchisong/301notes4.htm.
Greener et al. Poster by B. Greener, A. A. Hughes, N. P. Bannister. Smith & Nephew Research Centre, York Science Park, Heslington was presented at Wounds UK 2004, Harrogate.
Greener et al. paper published in Feb. 2005 in the Journal of Wound Care "Proteases and pH in chronic wounds".

* cited by examiner

Primary Examiner — David Browe
(74) Attorney, Agent, or Firm — Nelson Mullins Riley & Scarborough LLP

(57) ABSTRACT

A composition and method useful in promoting healing of a bleeding wound site. The composition preferably includes a substantially anhydrous acid form of a cation exchange resin, which when applied over blood, provides an antimicrobial against planktonic microorganisms and biofilms in the wound. The resin is also capable, when applied in sufficient quantities, of providing a continuing and persistent antimicrobial against planktonic microorganisms and biofilms through dehydration and ion exchange with cations present in the blood and other body fluids. When the resin has a concentration of at least 26 mg/ml, it provides a >3 log reduction in biological activity of MRSA, MRSE and *Pseudomonas aeruginosa*.

4 Claims, No Drawings

COMPOSITION AND METHOD FOR ARRESTING BLOOD FLOW AND FOR FORMING A PERSISTENT MICROBIAL BARRIER

CROSS-REFERENCE TO RELATED APPLICATION

The present application is a divisional of U.S. application Ser. No. 12/900,170, filed Oct. 7, 2010, which is hereby incorporated by reference herein in its entirety, including any figures, tables, nucleic acid sequences, amino acid sequences, or drawings.

FIELD OF THE INVENTION

This invention relates generally to hemostatic agents and particularly to topically applied powders or pastes that arrest bleeding and absorb exudates in wounds while providing a long lasting, persistent microbial barrier for planktonic microbes to prevent or eradicate biofilm formation on mammalian skin.

DESCRIPTION OF RELATED ART

Hemostatic agents are well known in the prior art. Patterson et al., 6,187,347, discloses a free flowing powder to arrest bleeding from a wound including the steps of (1) providing a substantially anhydrous compound of a salt ferrate which will hydrate in the presence of blood to produce $Fe^{+++}$ to clot blood and produce oxygen; and (2) applying this compound to the wound for a time sufficient to arrest blood flow and substantially reduce the microbial population by the presence of oxygen and forming a protective coating over the wound. In one embodiment, a cation exchange material is mixed with the salt ferrate to provide a protective coating over the wound for protection and enhanced healing. The salt ferrate provides the oxygen to substantially reduce the level of bacteria, virus and fungus at the wound site.

Weak acids, including benzoic acid, acetic acid, lactic acid, propionic acid, sorbic acid, fatty acids with 5 to 14 carbon chains are known as anti-microbial agents. The general guiding principles for antimicrobial properties are that they are generally weak acids and most work in the un-ionized form. It is customary to add a strong mineral acid to the weak acid antimicrobial to maintain a low pH (U.S. Pat. No. 6,472,358, Richter, et al.). Peracetic acid is an effective disinfectant which disintegrates to hydrogen peroxide and acetic acid. Peracetic acid works by oxidizing the outer cell membranes of microorganisms via the peroxy moiety. In practice, these antimicrobial agents are not known to be persistent since the weak acid is used up quickly in killing microbes. Persistency in antimicrobial action is defined as the ability to work under varied conditions whether in direct contact of antimicrobial agent with microbial colony before culturing with Luria Bertani (LB agent), or contacting the antimicrobial agent with LB agar first for 30 minutes and then adding the microbial colony. Persistency also pertains to having a reservoir of antimicrobial agent available to provide extended period of efficacy against microorganisms.

Organic and inorganic (mineral) cation exchange polymers are not normally known to provide antimicrobial properties by themselves. Strong base anion exchange resins in the $OH^-$ form were found to exhibit disinfection ability for pseudomonas stutzeri while a strong acid cation exchange resin in the $H^+$ form did not have disinfection ability (Colloids and Surfaces B: Biointerfaces Volume 7, Issues 1-2, 31 Jul. 1996, pages 91-100 authored by Nae Matsuda et al.). Antimicrobial properties are achieved when an antimicrobial agent is loaded unto an organic anion exchange resin or a zeolite. U.S. Pat. No. 7,147,845 teaches a silver-thiosulfate ion complex loaded unto an organic anion exchange resin that releases the silver complex in saline environment to provide antimicrobial protection. In U.S. Pat. No. 4,938,958, an antibiotic zeolite is prepared by replacing all or part of ion-exchangeable ions in zeolite with silver. U.S. Pat. No. 6,531,519 teaches the precipitation and encapsulation of a broad spectrum organic antimicrobial agent within the micropores of a synthetic (organic) ion exchange resin during suspension polymerization.

Hospitals often add active antimicrobial compounds such as ionic silver or chlorhexidine gluconate (CHG) to the secondary dressing to prevent biofilm formation and microbial infections from occurring. This is particularly critical when catheter procedures are used to evaluate the cardiac condition of a patient or a line is inserted into a patient for long term treatment (e.g., nutritional supplementation or chemotherapy). The secondary dressing is designed to be non-occlusive to allow free exchange of moisture from the covered surface through the dressing while simultaneously providing a physical barrier preventing microbial ingress. If the relative humidity underneath the dressing is too high, then the skin will over-hydrate and become irritated.

Biofilms

Bacteria form biofilms on surfaces. These films (slime) have a polysaccharide outer layer which protects the bacteria from external assault. The film often resembles a close-packed field of mushrooms wherein the top of the mushroom is the polysaccharide layer and the tunneling below the crown and near the stems allows fluid flow and nutrient access to the underlying bacteria.

Biofilms are typically hundreds to thousands of times harder to kill than planktonic (free flowing) bacteria. Biofilms can grow anywhere, but of particular concern is the biofilm that will grow along a catheter line entering the body, for example, through the skin of the arm into the brachial vein. It is well known that a biofilm can attach to the outer surface of the lumen and then grow down the lumen between the lumen and the skin and then along the lumen within the vein until the biofilm extends all the way to the end of the catheter. Once at the end, the biofilm fragments break off and change from biofilm into planktonic bacteria, infecting the host.

Many strategies have evolved to counteract this invasion route. One notable strategy is to use a CHG-impregnated disk (Biopatch) surrounding the catheter and to meter in CHG over 7 days to prevent formation of biofilms and subsequent CRBSIs (catheter related bloodstream infection).

An antimicrobial agent is expected to provide site sanitation. It is particularly advantageous when an antimicrobial agent also possesses: absorbent properties for serum exudates or blood to form a strong seal around the wound site; the ability to exchange with cations present in these fluids to release protons for a long lasting kill of planktonic microorganisms; persistent, long-lasting biofilm prevention; hemostatic properties; and wound healing properties.

U.S. Pat. No. 6,187,347 teaches the method of using a salt ferrate method for achieving hemostasis and site sanitation but not persistent biofilm prevention. U.S. Pat. No. 6,187,347 teaches the inclusion of the acid form of cation exchange resin to improve absorption to provide a protective coating and to provide acid to neutralize hydroxides to eliminate the stinging reaction caused by the hydrolysis of the salt ferrate.

U.S. Pat. No. 6,187,347

The U.S. Pat. No. 6,187,347 patent teaches that the combination of salt ferrate and an acid cation exchange resin produces $Fe^{+++}$ in a form which allows the iron cation to covalently interact with blood to effect coagulation and create a protective scab over the wound with antimicrobial properties. However, it has been found that the U.S. Pat. No. 6,187,347 teaching has flaws which raise costs:

1. Salt ferrate presents moisture sensitivity problems as the salt ferrate hydrolyses quickly in the presence of moisture, leading to limited shelf life unless protected by strong moisture barrier packaging material.

2. Hydrolysis of the salt ferrate produces hydroxide ions which are caustic to the skin manifested by a stinging sensation.

3. The antimicrobial action described in U.S. Pat. No. 6,187,347 is incomplete. The antimicrobial action is attributed solely to the salt ferrate which provides immediate antimicrobial activity. As will be shown below, the acid form of the cation exchange resin independently provides a continuing and persistent antimicrobial against both planktonic microorganisms and biofilms through a dehydration process and an ion-exchange process with the cations present in the body fluids.

4. The anhydrous powder also has an inherent effect of absorbing moisture, either as exudate or humidity. This keeps the moisture level beneath the secondary dressing below the irritation level.

U.S. Pat. No. 6,187,347 does not teach hemostatic and antimicrobial properties derived solely from the use of the acid form of a cation exchange resin. Furthermore, it does not teach that the acid form of a cation exchange resin provides persistent biofilm prevention and eradication properties by release of protons from exchange with cations present in exudates, serum or blood.

There are a litany of benefits that hospitals require when treating hospital-induced wounds such as catheters:

1. Stop the bleeding rapidly and reliably (no re-bleeds).
2. Prevent microbial contamination of the wound site.
3. Prevent biofilms from migrating down the line into the bloodstream (catheter related bloodstream infections (CRBSI)). Biofilms can form on either side of the lumen (i.e., external or internal).
4. Maintain healthy skin.
5. Reduce costs.

The prior art is directed towards stopping bleeding rapidly and reducing the concentration of microbes at the wound surface. The art does not identify ways to maintain low microbial count after the bleeding stops. In fact, a second product is used to persistently maintain low microbial counts. There is clearly a need for a product that could deliver all the hospital-demanded benefits in one product.

The foregoing examples of the related art and limitations related therewith are intended to be illustrative and not exclusive. Other limitations of the related art will become apparent to those skilled in the art upon a reading of the specification and a study of the drawings.

BRIEF SUMMARY OF THE INVENTION

This invention is directed to a composition and method of using the acid form of a cation exchange resin for stopping bleeding, absorbing exudates, sanitizing the wound surface, creating a persistent, long lasting zone of microbial inhibition against biofilms while maintaining healthy skin. This powder composition is in fluid communication with a physical barrier to flow wherein the depth of the free flowing powder is sufficient to provide a reservoir for continual release of protons. It is also directed towards creating a barrier to prevent microbial migration across the barrier to the surface of mammalian skin.

The hydrogen form of cation exchange resin by itself provides hemostatic properties by strong dehydration of blood concentrating the clotting factors to form a strong seal around the wound site. At the same time, it provides continuous and persistent antimicrobial properties against both planktonic microorganisms and biofilm. The long lasting antimicrobial action is achieved by release of protons from exchange with cations present in exudates, serum or blood. The hemostatic and antimicrobial properties of the hydrogen form of cation exchange resin are not taught by U.S. Pat. No. 6,187,347. In the case of a weak acid antimicrobial such as benzoic acid or acetic acid, there is no exchange with cations in body fluids to produce protons which is an important ion in challenging microorganisms.

The following embodiments and aspects thereof are described and illustrated in conjunction with systems, tools and methods which are meant to be exemplary and illustrative and not limiting in scope. In various embodiments one or more of the above-described problems have been reduced or eliminated while other embodiments are directed to other improvements.

DETAILED DESCRIPTION OF THE INVENTION

The following is a brief explanation of how the acid form of a cation exchange resin provides hemostasis and antimicrobial action.

1. The dry resin absorbs four times its weight of water. In contact with blood, it absorbs the water in the blood quickly and concentrates the clotting factors to form a strong seal to stop bleeding. Likewise, a strong seal is formed in contact with serum or exudates.

2. The blood contains sodium, potassium, magnesium and calcium cations represented as $M^+$ and $M^{++}$, respectively. The cations exchange with the acid ion-exchange resin to yield protons.

3. $M^+ + R-H \rightarrow R-M + H^+$

4. $M^{++} + R-H \rightarrow R-M + 2\ H^+$ a. The pH in the seal formed with blood falls to <3 with the liberation of protons.

Microbes are 80 to 90% water and contain sodium and potassium cations. The resin is capable of absorbing four times its weight in moisture. When a microbe passes through the resin, the microbe loses critical moisture in a low pH environment and dies. The cations necessary for microbial viability are extracted from the microbe and exchanged by the resin for a proton. The combination is lethal.

Microbes come in different shapes, but all have an exterior cell wall which provides structure to the organism. Without wishing to be bound, when the microbe is in contact with resin, there is an entropy driving force for cations to leave the microbe and enter the resin and be replaced with acidic protons. The driving force is analogous to an osmotic pressure difference, except the driving force is based on the cation concentration difference between the interior of the microbe and the interior of the resin. When this cation extraction occurs, the structure of the organism changes and its viability is compromised. Even after the resin has absorbed all the water it can, there is a continuing antimicrobial effect because the resin can still absorb potassium and sodium ions and destroy the microbe's reproduction capability. The mechanism of action is considerably different than described in the U.S. Pat. No. 6,187,347 patent and for weak acid antimicrobial agents such as sorbic acid and acetic acid.

Example 1

The adhesiveness and strength of a seal formed by fresh human blood and a dry ion exchange resin—hydrogen form of sulfonated, 2% crosslinked polystyrene resin was evaluated. A 0.1 mL sample of fresh human blood was placed on a plastic boat with a one square inch circular template. The blood was spread evenly on the template. 400 mg of the dry resin was poured on top of the blood. After 90 seconds, the excess resin was discarded, after which a seal formed from coagulated blood and resin was observed. After scrapping with a 6 mm wide spatula to remove weakly adhered parts of the seal, 30 mg of the seal was retained, indicating that a strong and adhesive seal was formed.

Example 2

The in vitro antibacterial activity of a dry ion exchange resin (hydrogen form of sulfonated, 2% crosslinked polystyrene resin) was evaluated. Twice washed liquid cultures were resuspended in sterile water to provide a concentration of approximately $10^8$ CFU/ml for each strain. The liquid cultures were added to 50 ml conical tubes containing the dry resin that had been pre-weighed to produce the desired concentration upon addition of 1 mL of bacterial suspension. The samples were vortexed and allowed to stand undisturbed for 30 minutes at room temperature. Each sample was serially diluted and quantitative culture on Luria-Bertani (LB agar) was performed. The hydrogen resin demonstrated significant bactericidal activity. No organisms were recovered by quantitative culture at exposure levels of 5 mg/mL. Dose responses were seen. The estimated dose required to effect 99% killing of three bacteria are presented in Table 1 below.

TABLE 1

Mg/mL of hydrogen form of sulfonated 2% crosslinked polystyrene resin (hydrogen resin) required for 99% bacterial killing

| Organism | Mg/mL of hydrogen resin |
|---|---|
| Pseudomonas aeruginosa PA7 | 0.83 ± 0.04 |
| Staphylococcus epidermidis MRSE (ATCC #700565) | 1.87 ± 0.08 |
| Staphylococcus aureus MRSA (ATCC #43300) | 4.22 ± 0.26 |

All values reported as mean ±standard error.
Thus, the hydrogen resin is a powerful antibacterial agent against at least two of the most antibiotic resistant bacteria commonly occurring in hospital settings, i.e., MRSA and MRSE.

Example 3

This example demonstrates that the same hydrogen resin mentioned in Example 2 has persistence in vitro antibacterial activity. Hydrogen resin was added to 10 mL of Luria-Bertani (LB) media and allowed to hydrate for 30 minutes with mixing. Single bacterial colonies were added and placed in an incubator at 37° C. and 200 RPM for 8 hours. Bacterial proliferation was measured as the change in sample turbidity during incubation. The hydrogen resin inhibited bacterial growth at both 1 and 5 mg/mL as measured by liquid culture turbidity. The inhibition was significantly greater at 5 mg/mL compared to 1 mg/mL (see Table 2 below).

TABLE 2

Persistency of in vitro antibacterial activity of hydrogen form of sulfonated 2% crosslinked polystyrene resin (reported as reduction in bacterial colonies)

| Organism | 1 mg/mL | 5 mg/mL |
|---|---|---|
| Pseudomonas aeruginosa PA7 | 80% reduction | 95% reduction |
| Staphylococcus epidermidis MRSE (ATCC #700565) | 30% reduction | 99% reduction |
| Staphylococcus aureus MRSA (ATCC #43300) | 15% reduction | 99% reduction |

Example 4

The ability of hydrogen form of sulfonated 2% crosslinked polystyrene resin (hydrogen resin) to eradicate biofilm was studied with the Calgary Biofilm Device (CBD) (reference—Laila Ali et al., "Investigating the suitability of the Calgary Biofilm Device for assessing the antimicrobial efficacy of new agents", Bioresource Technology 97 (2006) 1887-1893). The CBD assay was developed by the University of Calgary as a simple assay to reliably culture 96 identical biofilms at a time. The CBD assay provides rapid testing of compounds for anti-biofilm activity. The hydrogen resin was evaluated for anti-biofilm activity against MRSA, MRSE and Pseudomonas aeruginosa using the CBD. The results are summarized in Table 3 below.

TABLE 3

Biofilm eradication by the hydrogen form of sulfonated 2% crosslinked polystyrene resin (hydrogen resin)

| | Hydrogen resin concentration in mg/mL | | |
|---|---|---|---|
| Microorganism | MRSA | MRSE | *Pseudomonas aeruginosa* |
| MIC breakpoint | ≤26 | ≤26 | ≤26 |
| MBC breakpoint | ≤26 | ≤26 | ≤26 |
| MBEC breakpoint | ≤26 | ≤26 | 53 |
| Minimum concentration that kills biofilms with logR ≥ 3 | 26 | 26 | 26 |

Legend:
MRSA = Methicillin-Resistant *Staphylococcus aureus* 399
MRSE = Methicillin-Resistant *Staphylococcus epidermidia* ATCC 35984
P aeruginosa = Pseudomonas aeruginosa ATCC 27853
MIC—minimum inhibitory concentration against planktonic microorganism
MBC—minimum bactericidal concentration against planktonic microorganism
MBEC—minimum biofilm eradication concentration
Breakpoint—concentration at or below
logR—log reduction The minimum inhibitory concentration (MIC) and minimum bactericidal concentration (MBC) breakpoints against all three planktonic microorganisms are the same at 26 mg/mL. The minimum biofilm eradication concentration (MBEC) breakpoint is surprisingly the same at 26 mg/mL for MRSA and MRSE and about twice the concentration at 53 mg/mL for *Pseudomonas aeruginosa*.

When biofilms are formed, they are difficult to remove as they show an increased resistance to biocides and antibiotics when compared to planktonic microorganisms. Studies have shown greater than a hundred to a thousand fold resistance to antibiotics of biofilms compared to the same bacteria in planktonic state. Therefore the identical or similar concentration breakpoints between MBEC and MIC/MBC for hydrogen resins are very significant.

The results suggest that the hydrogen resin is able to rob the water from the biofilm, that ion exchange is proceeding to free up the proton, and that the proton is able to penetrate through the complex matrix of the biofilm to inactivate and destroy it. The concentration of hydrogen resin required to provide a .gtoreq.3 log reduction in activity of the three biofilms is equal at 26 mg/mL. At 26 mg/mL, hydrogen resin provided 3.2 log reduction of MRSA biofilm, 3.5 log reduction of MRSE biofilm and 4.5 log reduction of *Pseudomonas aeruginosa* biofilm.

Example 5

Eight concentrations of dry hydrogen resin powder were studied in the Calgary Biofilm Device (CBD) as shown in Table 4 below. This was achieved by weighing the indicated weights into different wells of the CBD. Next, a precise amount (microliter, ul) of saline was pipetted into the corresponding wells of the CBD following the quantities specified in column 1 of Table 4. The resulting concentrations in mg/mL are shown in column 2.

TABLE 4

The ability of hydrogen form of a sulfonated 2% crosslinked polystyrene resin to eradicate biofilm

| mg/ul $H^+$ resin/saline | mg/mL $H^+$ resin/saline | MRSA | MRSE | *Pseudomonus aeruginosa* |
|---|---|---|---|---|
| | | | Log Reduction | |
| 160/0 | pure powder, no saline | 3.2 | 3.48 | 5.98 |
| 75/106 | 745 | 3.2 | 3.48 | 5.63 |
| 50/138 | 384 | 3.2 | 3.48 | 5.63 |
| 38/153 | 255 | 3.2 | 3.48 | 5.98 |
| 25/169 | 154 | 3.2 | 2.98 | 5.98 |
| 15/181 | 88 | 2.85 | 3.48 | 5.98 |
| 10/189 | 58 | 3.2 | 3.48 | 5.98 |
| 5/194 | 26 | 3.2 | 3.48 | 4.48 |

At the lower concentrations (26, 58, 88 and 154 mg/mL), the hydrogen resin has fully absorbed the saline and excess saline is available outside the swelled resin phase. The excess saline is greatest at 26 mg/mL and lowest at 154 mg/mL. At 255 mg/mL, the resin is fully absorbed with saline with no excess saline is available. At 384 mg/mL, the resin is only hydrated to 69% assuming the resin is uniformly hydrated. At 745 mg/mL, the resin is only 35% hydrated. The extreme case is where the well contains only 160 mg resin with no saline. The assay was run in triplicate. When challenged with MRSA biofilm (see column 3) or MRSE biofilm (column 4), the whole concentration range of hydrogen resin showed a log reduction close to 3 or higher. When challenged with *Pseudomonas aeruginosa* biofilm (column 5), the lowest concentration of 26 mg/mL gave a log reduction of 4.48 while the rest gave log reductions of 5.6 or higher.

The results indicate that hydrogen resin eradicates biofilm very efficiently even at a very low concentration of 26 mg/mL. Furthermore, the data suggest that excess capacity or persistency for biofilm eradication is available at higher concentrations. In particular, at the concentrations where the hydrogen resin is not fully hydrated, there is excess capacity or persistency to extract water and cations from any new biofilm that may form after the first wave of biofilm has been destroyed. At the extreme, a completely dry hydrogen resin provides the greatest capacity for repeatedly killing biofilms, increasing its persistency.

This finding can be applied to a bleeding or exuding wound from a vascular access procedure or percutaneous catheters and tubes where excess dry hydrogen resin is applied to stop bleeding or to form a strong seal around wounds. Once the powder dressing is applied, a secondary dressing is applied over the powder dressing to keep the resin above the seal dry as a reservoir for preventing biofilms from forming and for continually eradicating planktonic cultures and biofilms. The persistency for biofilm eradication is determined by the height and quantity of the reservoir of dry hydrogen resin available on the wound site.

ALTERNATE EMBODIMENTS

In another embodiment, a powder containment device (PCD) is employed to build the height and to contain the dry hydrogen resin powder within the device. In another embodiment, the resin is applied over minor-to-severely bleeding wounds such as surgical wounds including post-operative, post-suturing, donor sites and dermatological wounds to stop bleeding as well as to provide a microbial barrier to prevent infection. In yet another embodiment of the invention, the resin is used for managing exuding wounds such as pressure ulcers, venous ulcers, diabetic ulcers and arterial ulcers taking advantage of its microbial barrier properties. In yet another embodiment, the optional inclusion of other cationic forms (such as silver and alkali metal cations and quarternary ammonium cations) of the ion exchange resin with the hydrogen form of the resin may further extend its antimicrobial properties.

Other embodiments of this invention include the optional presence of other substances such as hydrophilic inorganic or organic polymers, clays, gums, natural polysaccharides, oxidized cellulose, regenerated cellulose, chitosan and the like that, when added to the protonic ion exchange resin, can impart adhesive and strengthening properties to the seal formed with blood.

While a number of exemplary aspects and embodiments have been discussed above, those of skill in the art will recognize certain modifications, permeations and additions and subcombinations thereof. It is therefore intended that the following appended claims and claims hereinafter introduced are interpreted to include all such modifications, permeations, additions and subcombinations that are within their true spirit and scope.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method of promoting healing of a wound having human blood comprising the steps of:
   providing a seal-forming composition consisting of a substantially anhydrous acid form of a cation exchange resin that, when forming a seal with the wound, results in the seal having a pH less than 3;
   applying an amount of the seal-forming composition to the human blood, said amount sufficient to form a microbial barrier seal over the wound; and
   maintaining the seal-forming composition in place over the wound for a time sufficient to allow formation of a reservoir of the seal-forming composition to promote healing of the wound.

2. A method of promoting healing of a wound having human blood comprising the steps of:
   providing a seal-forming composition consisting of a substantially anhydrous acid form of a cation exchange resin that, when forming a seal with the wound, results in the seal having a pH less than 3;
   applying an amount of the seal-forming composition to the wound, said amount sufficient to form a microbial barrier seal over the wound;
   maintaining the seal-forming composition in place over the wound for a time sufficient to allow formation of a reservoir of the seal-forming composition to promote healing of the wound; and
   discarding excess seal-forming composition that is above the microbial barrier.

3. The method of promoting healing of a wound having human blood as set forth in claim 1 wherein the seal-forming composition is applied to the wound in an amount to provide a resin concentration of at least 26 mg of acidic cation exchange resin per ml of blood.

4. The method of promoting healing of a wound having human blood as set forth in claim 2, wherein the seal-forming composition is applied to the wound in an amount to provide a resin concentration of at least 26 mg of acidic cation exchange resin per ml of blood.

* * * * *